United States Patent [19]

Shiner et al.

[11] Patent Number: 4,997,372

[45] Date of Patent: Mar. 5, 1991

[54] MAGNETIC DENTAL RETENTION APPLIANCE

[75] Inventors: James R. Shiner; Roger E. Rule, both of San Diego, Calif.

[73] Assignee: JS & R Inc., San Diego, Calif.

[21] Appl. No.: 428,369

[22] Filed: Oct. 27, 1989

[51] Int. Cl.[5] ............................................. A61C 13/235
[52] U.S. Cl. ................................................... 433/189
[58] Field of Search .......................................... 433/189

[56] References Cited

U.S. PATENT DOCUMENTS

| | | |
|---|---|---|
| 711,324 | 10/1902 | Lacy . |
| 866,304 | 9/1907 | Roach . |
| 2,149,048 | 2/1939 | Freedman ................. 32/2 |
| 2,543,773 | 3/1951 | Goldschmidt .............. 32/2 |
| 2,555,392 | 6/1951 | Bierbach et al. ........... 32/2 |
| 2,555,403 | 6/1951 | Freedman ................. 32/2 |
| 2,616,174 | 11/1952 | Goldsmith ................. 32/2 |
| 2,709,301 | 5/1955 | Goldsmith ................. 32/2 |
| 2,732,621 | 1/1956 | Pelzmann .................. 32/2 |
| 2,803,879 | 8/1957 | Cook ........................ 32/2 |
| 3,141,214 | 7/1964 | Bey ......................... 24/201 |
| 3,514,859 | 6/1970 | Peterson .................. 32/2 |
| 3,646,676 | 3/1972 | Mitchell ................... 32/2 |
| 3,787,975 | 1/1974 | Zuest ....................... 32/5 |
| 3,798,770 | 3/1974 | Mitchell ................... 32/2 |
| 4,184,252 | 1/1980 | Krol ......................... 433/172 |
| 4,202,097 | 5/1980 | Erlich-Deguemp ........ 433/189 |
| 4,209,905 | 7/1980 | Gillings ................... 433/189 |
| 4,242,089 | 12/1980 | Sasaki ..................... 433/189 |
| 4,302,189 | 11/1981 | Gillings ................... 433/189 |
| 4,359,318 | 11/1982 | Gittleman ................ 433/173 |
| 4,431,419 | 2/1984 | Portnoy ................... 433/189 |
| 4,488,875 | 12/1984 | Niznick ................... 433/173 |
| 4,508,507 | 4/1985 | Jackson ................... 433/189 |
| 4,626,213 | 12/1986 | Shiner et al. ............ 433/173 |
| 4,723,913 | 2/1988 | Bergman .................. 433/173 |
| 4,824,371 | 4/1989 | Deutsch et al. .......... 433/189 |
| 4,857,873 | 8/1989 | Gillings ................... 433/189 |

FOREIGN PATENT DOCUMENTS

3140464A1 10/1981 Fed. Rep. of Germany .
62-231653 10/1987 Japan .
WO82/03547 10/1982 PCT Int'l Appl. .

Primary Examiner—Cary E. Stone
Attorney, Agent, or Firm—Juettner Pyle Lloyd & Verbeck

[57] ABSTRACT

A magnetic dental retention appliance comprises a magnet containing subunit to be embedded in a denture, a magnetizable keeper subunit to be secured within the jaw structure of the patient for retaining the denture in the mouth, and a transmucosal insert to be implanted in the patient's jawbone for anchoring the keeper subunit to the patient's jaw; the transmucosal insert being formed of a material ideal for implantation and diverse from the requisite ferromagnetic material of the magnetizable keeper subunit; the insert being isolated from the keeper subunit by an interposed insulating member which effectively curtails or prevents corrosive galvanic action between the two, thereby facilitating use of the most ideal materials of construction for the subunits and the insert.

12 Claims, 1 Drawing Sheet

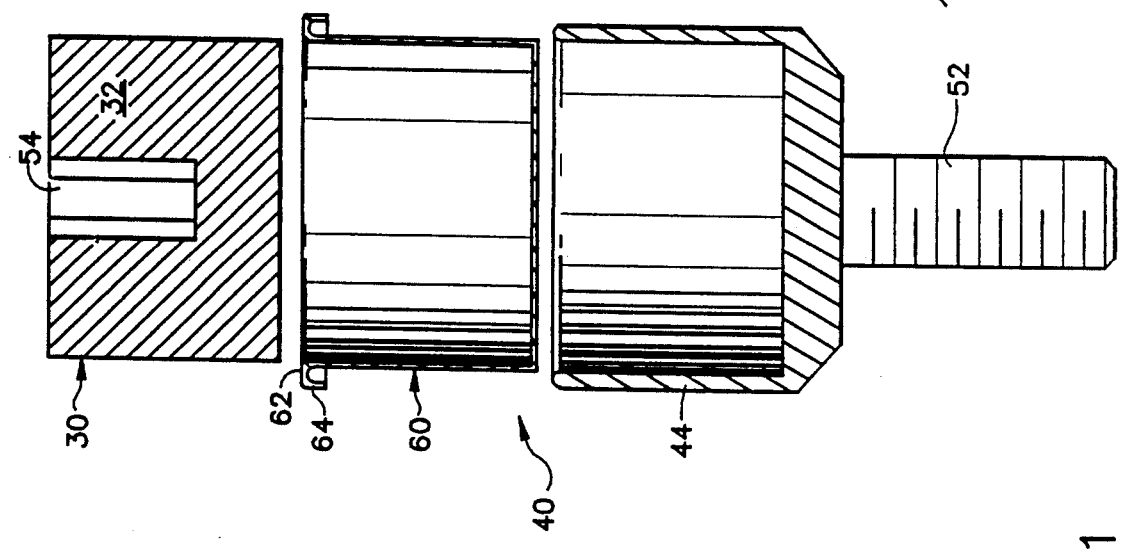
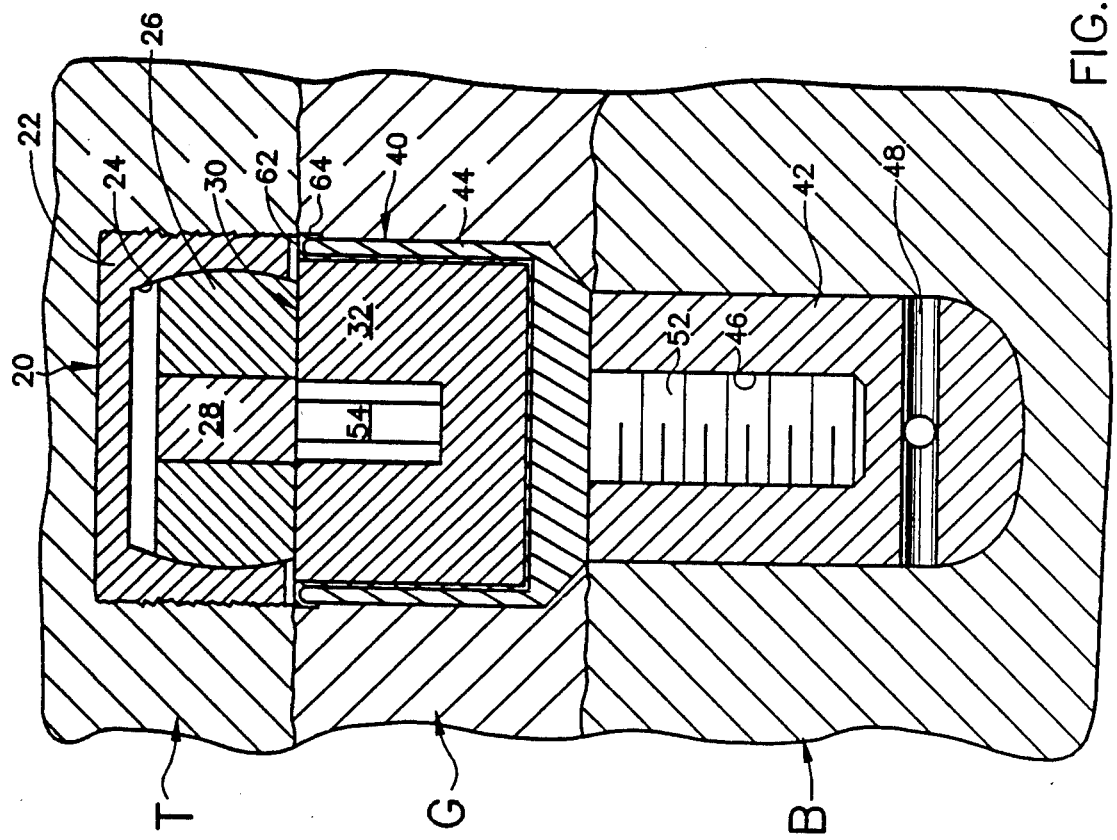

MAGNETIC DENTAL RETENTION APPLIANCE

TECHNICAL FIELD

The present invention relates to dental appliances which employ magnetic retention means.

BACKGROUND ART

The many problems associated with adhering dentures to gum tissue by means of adhesives has resulted in the development of various retention means based on the use of magnets. Examples of dental appliances of the general type can be found in U.S. Pat. Nos. 4,184,252, 4,209,905, 4,302,189 and 4,431,419; in PCT International Publication WO 82/03547, dated Oct. 28, 1982; and in U.S. Pat. No. 4,626,213 in which one of the present applicants is a named inventor.

In magnetic dental retention appliances of the general character, wherein a denture is retained in place through the interaction of a magnet embedded in the denture and a magnetizable keeper embedded in the patient's mouth, it has been inadvisable to use different metallic materials of construction because of the corrosive galvanic action established between such metals in the presence of the electrolytic medium constituted by the saliva in the mouth. This has deterred the use of some materials of construction in magnetic dental retention appliances, despite the advantages such materials may offer. In general, and as a practical matter, only ferromagnetic materials may safely be employed; the preferred material being ferromagnetic stainless steel.

The inability to use diverse materials is a particularly frustrating obstacle to the use of optimum materials of construction in dental restorations requiring implantation of retention means within the bone structure of the jaw beneath the tissues of the gum and the mucous membrane defining the gingival margin of the gum structure.

While galvanic contact occuring in the electrolytic medium of the saliva in the mouth is referred to in International Publication WO 82/03547, the Publication does not offer a solution to the above discussed deficiencies in prior magnetic dental appliances.

SUMMARY OF THE INVENTION

The object of the present invention is to provide an improved magnetic dental retention appliance accomodating the use of diverse metallic components in its construction, and in particular, a dental implant appliance accomodating use within the bone structure and gum tissue of the mouth of materials of construction most ideally suited for use in that environment even though the same are diverse from the ferromagnetic materials required for retention purposes.

In accordance with the present invention, one of the subunits of the magnetic assembly, preferably the magnetizable keeper, is secured within a transmucosal insert to be embedded in the jaw of the patient; the transmucosal insert bridging the mucosal tissue and gingival margin of the gum and being constructed of a material, such as titanium, which is different from that of the keeper and which enjoys the particular advantage of mutually reciprocal immunity in relation to the structure of the jaw and the tissues and excretions of the mouth; the insert being isolated from the keeper and the remainder of the magnetic assembly by an isolation member interposed between the keeper and the transmucosal insert, thereby to prevent, or at the very least inhibit, electrolytic currents and their deleterious corrosive consequences.

By virtue of its isolation from the magnetic assembly, and its consequent elimination of galvanic action between diverse metals, the transmucosal insert of the invention facilitates the use in dental reconstructions of magnetic appliances including implants of materials that have mutually reciprocal immunity with the tissues of the mouth and jaw, and that can be constructed of materials ideally suited for implantation in the bone structure of the jaw.

The invention thus obviates the necessity for and the disadvantages consequent from exclusive reliance upon ferromagnetic materials of construction in the manufacture, assembly, installation and/or implantation of magnetic dental retention appliances.

These and other features and advantages of the invention will become apparent from the following detailed description, considered in conjunction with the accompanying drawings.

BRIEF DESCRIPTION OF THE DRAWINGS

FIG. 1 is an illustration in vertical section of a denture or artificial tooth retained in the lower jaw or mandible of a patient by a magnetic retention appliance provided in accordance with the invention, the appliance including an implant in the mandible bone and a transmucosal extension projecting through the gum and mucous membranes of the mandible; and FIG. 2 is an exploded vertical section of component parts of a preferred embodiment of the transmucosal insert provided in accordance with the invention.

DETAILED DESCRIPTION

In FIG. 1 of the drawings, B indicates the bone of the lower jaw or mandible of a dental patient, G the gum tissue of the mandible, and T an artificial tooth or denture to be retained by the mandible proximate the gingival margin of the gum. Though shown in relation to the mandible, the improved retention appliance of the invention is equally applicable to dental restorations in the upper jaw or maxilla, as may be viewed simply by inverting FIG. 1.

As disclosed in U.S. Pat. No. 4,626,213, the magnetic components of the retention appliance consist of a socket ring 22 having a socket 24 therein the side walls of which are partially spherical; magnetizable leg elements 26 having partially spherical side walls complementary to the spherical side walls of the socket 24 and retained within the socket ring 22 by virtue of such complementary spherical walls; a bar magnet 28 mounted centrally between the leg elements 26; and a separable magnetizable keeper 32. The ring 22, leg elements 26 and keeper 32 are all ferromagnetic, preferably stainless steel, and the magnet 28 is preferably a samarium-cobalt or neodymium iron boron rare earth magnet.

These magnetic components may be considered as comprising two subunits, namely, a first subunit 20 comprised of the socket ring 22, the leg elements 26 and the magnet 28, and a second subunit 30 comprised of the keeper 32. The two subunits are the subject of U.S. Pat. No. 4,626,213. The present invention is directed to the manner of installing one of the subunits in the mouth. Either subunit may be installed in the patient's mouth. However, it is usually more expedient and convenient, and less disturbing to the patient, to install the magnet subunit 20 in the denture and the keeper subunit 30 in the patient's mouth. Consequently, the present invention will be described in terms of the usual or customary practice, i.e., with the magnetizable keeper subunit 30 installed in the patient's mouth, but with the understanding that the invention would also accomodate installation in the mouth of the first or magnet subunit 20.

As illustrated in FIG. 1, the socket ring 22 is customarily embedded or fixedly secured within the denture or artificial tooth T, and may be cemented or cast therein or may be removably inserted therein by means of an external screw thread as shown in U.S. Pat. No. 4,626,213. As is also shown in the patent and other prior art disclosures, the keeper 32 is customarily embedded in the retained root of an existing tooth by means of an integral shank threaded or cemented into a hole drilled in the root.

The spherical socket 24 mounts the permanent magnet 28 for swiveling movement and thereby facilitates precise alignment of the juxtaposed flat faces of the magnet and the keeper so that the magnet remains in full, face-to-face magnetic contact with the mating flat face of the keeper, even during articulation and mastication, thereby to insure continuous and firm retention of the denture in the mouth of the wearer. Because of its advantages, the illustrated spherical socket and permanent magnet subunit 20 is recommended for use in practice of the present invention, although other magnetic subunits may be used if desired.

In accordance with the present invention, the other or keeper subunit 30 is mounted within the mouth of the patient by means of a transmucosal insert 40. In its preferred embodiment, the insert comprises an implant portion or member 42 and a separable transmucosal extension member or portion 44. However, the transmucosal insert could be constructed as a unitary one-piece member if desired.

In the preferred embodiment, the implant portion 42 of the insert 40 comprises a cylindrical post having a diameter in the order of about 0.15 inch and a length in the order of about 0.40 inch. A threaded bore 46 extends axially downward from the top surface of the post to accomodate the assembly of the extension 44 with the post. The post is provided adjacent its bottom with a plurality of transverse recesses or cross-bored holes 48 and its bottom is preferably rounded to somewhat hemispherical form. The post 42 is adapted to be implanted in the boney structure B of the jaw by drilling into the bone a hole of substantially the same size as the post and inserting the post in the hole. The depth of the hole is preferably such that the upper surface of the post is substantially flush with the upper surface of the bone. During the subsequent healing process, the bone grows tightly around the post and into or through the recesses or holes 48 therein, thereby intimately to bond the implanted post within the bone.

The extension 44 of the insert 40 comprises a cup-shaped member of a larger diameter than the post and including an axially downwardly extending externally threaded stud 52 for threaded mounting in the post 42. The cup 44 mounts the keeper 32 so that the upper flat face of the keeper will be exposed at the gingival margin of the gum for cooperation with the magnet subunit 20. To facilitate threaded attachment of the cup 44 to the post 42, the keeper 32 is preferably provided with an upwardly open polygonal socket 54 for reception of a tool, such as an Allen wrench, of complementary shape. The cup 44 may suitably be about 0.20 inch in diameter and about 0.125 inch long thereby to accomodate a keeper 32 having an upper flat face diameter in the order of about 0.17 inch, which is adequate to provide for firm retention of the tooth or denture T.

Instead of being threaded, the stud 52 could have a circumferentially grooved exterior surface and be cemented in the post. However, the screw threaded arrangement is preferred as it accomodates removal and/or replacement of the keeper subunit without disturbing the implant 42.

The material of construction presently deemed best suited for implantation in the patient's jawbone and gum is titanium. However, use of titanium has not usually been best advised because of the diversity between it and the stainless steel components required for the magnetic subunits, and the consequent likelihood of the development of corrosive electrolytic currents between the diverse metals. To eliminate or effectively curtail the problem, and thereby accomodate the safe use of diverse metals, particularly stainless steel and titanium, the present invention provides means for effectively isolating the implant components from the magnetic components of the appliance.

In accordance with the invention, a thin walled cup-shaped liner 60 of insulating material is provided to completely line the interior surfaces of the cup 44 and the side and bottom walls of the keeper 32 thereby to isolate the keeper from the cup and mitigate the potential for current flow between them. Also, the liner 60 may include an outwardly extending flange 62 at its upper end which overlies the upper edge of the cup 44 thereby to insure isolation of the cup 44 from the magnet subunit 20 as well as the keeper subunit 30. To even further insure total isolation, the flange 62 of the liner 60 may include a downwardly extending annular extension 64 which overlies the upper exterior side wall surface portions of the cup 44 and extends downwardly past the gingival margin and into the tissue of the gum so that the implant components are completely shielded and isolated from the magnetic components by the combination of the gum tissue and the isolating liner 60.

By virtue of the described construction, and the advantages afforded by the insulating liner 60, the metallic components of the appliance may be constructed of the materials best suited for respective functions, i.e., ferromagnetic stainless steel for the magnetic retention components, and titanium for the transmucosal components. The liner 60 may suitably have a wall thickness of about 0.005 to 0.010 inch and is preferably formed of Delrin, Nylon, acrylic or a similar material because such materials offer good insulating characteristics, are inert, are suitable for use in the mouth, and are readily fabricated into the form illustrated and described. The keeper subunit 30 is assembled with the liner 60 and the cup 40 by press fitting the same together into a unitary assembly.

The assembly comprised of the keeper, liner and cup may then readily be attached to and detached from the implanted post 42 by threading the stud 52 into and out of the bore 46. Formation of the implantation members 42 and 44 as separable members, as herein described, facilitates the implantation and healing process, and also accomodates ready removal of the keeper subunit 30 without disturbing the implant 42 should it become necessary or desirable to remove or replace the magnetic subunit.

The invention thus provides significant improvements in magnetic dental retention appliances, particularly retention appliances requiring implantation in the bone beneath the gum, and facilitates the use of diverse materials of construction in the fabrication of such appliances. The objects and advantages of the invention have thus been shown to be attained in a convenient, economical and facile manner.

While the preferred embodiment of the invention has been herein illustrated and described, it is to be appreciated that various changes, rearrangements and modifications may be made therein without departing from the scope of the invention, as defined by the appended claims.

What is claimed is:

1. In a magnetic dental retention appliance having a magnet subunit and a keeper subunit each including ferromagnetic materials of construction, one of which subunits is to be mounted in a dental restoration and the other of which is to be mounted in a dental patient's mouth to retain the restoration in the mouth, the improvement comprising:
   a mounting member for mounting one of the subunits in the mouth, said member being constructed of a metallic material diverse from that of the subunit and being shaped for conformable reception of the subunit; and
   a dielectric insulating liner between said member and the subunit, said liner separating all adjoining surfaces of said member and the subunit and electrically isolating said member from the subunit to mitigate flow of electrolytic currents between them.

2. The improvement of claim 1, wherein the one subunit includes ferromagnetic stainless steel and said mounting member is comprised of titanium.

3. The improvement of claim 1, wherein said liner is comprised of a material selected from the group of materials comprising Delrin, Nylon, acrylic and similar materials.

4. The improvement of claim 1, wherein said mounting member is of cup-shape for conformably receiving the subunit therein, and said liner is of a cup-shape complementary to the cup-shape of said member and includes at its upper edge an outwardly extending flange overlying the upper edge of said mounting member.

5. The improvement of claim 1, wherein said mounting member is of cup-shape for conformably receiving the subunit therein, said liner is of a cup-shape complementary to the cup-shape of said member and includes at its upper edge an outwardly extending flange and an annular extension depending downwardly from said flange, said flange and annular extension encompassing the upper marginal edge portions of said mounting member and isolating said edge portions from the subunits.

6. In a magnetic dental retention appliance having a magnet subunit and a keeper subunit each including ferromagnetic materials of construction, one of which subunits is to be mounted in a dental restoration and the other of which is to be mounted in a dental patient's mouth to retain the restoration in the mouth, the improvement comprising:
   a transmucosal insert to be imbedded in the tissues of the patient's jaw for mounting one of the subunits in the patients mouth, said insert including a cup-shaped portion of a size to conformably receive the subunit and formed of a metallic material diverse from that of the subunit, said cup-shaped portion having a free upper edge to be located proximate the gingival margin of the gum tissue in the patient's mouth; and
   a cup-shaped dielectric insulating liner complementary to the interior of said cup-shaped portion and the exterior of the subunit and conformably inserted within the cup-shaped member between the member and the subunit, said liner separating all adjoining surfaces of said insert and the subunit and electrically isolating said insert from the subunit to mitigate flow of electrolytic currents between them.

7. The improvement of claim 6, wherein said liner includes at its upper edge an outwardly extending flange overlying the upper edge of said cup-shaped portion.

8. The improvement of claim 7, wherein said liner also includes an annular extension depending downwardly from said flange for extension from said flange into the tissue of the gum below the gingival margin, said flange and annular extension encompassing the upper marginal edge portions of said cup-shaped portion and isolating said edge portions from the subunits.

9. The improvement of claim 6, wherein said transmucosal insert includes a lower portion for implantation in the jawbone of the patient and a transmucosal portion extending through the gum tissue from the jawbone to the gingival margin of the gum.

10. The improvement of claim 9, wherein said lower portion is of a diameter smaller than the diameter of the transmucosal portion to facilitate implantation of said lower portion in the bone, and wherein said transmucosal portion includes said cup-shaped portion and is of a diameter larger than said lower portion to accomodate fabrication of said cup-shaped portion in a size adequate to conformably receive the subunit.

11. The improvement of claim 9, wherein said lower portion is separate from said transmucosal portion and said lower portion and said transmucosal portion include means facilitating insertion of said transmucosal portion without disturbing the implantation of said lower portion in the jaw.

12. The improvement of claim 6, wherein said transmucosal insert is comprised of a post for implantation in the jawbone of the patient and a transmucosal extension for extension through the patient's gum tissue from said post to the gingival margin of the gum, said transmucosal portion including said cup-shape portion at its upper end proximate to the gingival margin, said post being separate from and of a smaller diameter than said transmucosal extension to facilitate implantation of said post in the bone, said transmucosal extension being of a larger diameter than said post to accomodate fabrication of said cup-shape portion of a size to receive the subunit, said post and transmucosal extension including cooperable fastening means accomodating attachment of said transmucosal extension to said post and facilitating removal of said transmucosal extension without disturbing the implantation of said post in the bone.

* * * * *